United States Patent
Yang et al.

(10) Patent No.: US 12,303,283 B2
(45) Date of Patent: May 20, 2025

(54) DECISION SUPPORT SYSTEM AND METHOD THEREOF FOR NEUROLOGICAL DISORDERS

(71) Applicant: Neurobit Technologies Co., Ltd., Taipei (TW)

(72) Inventors: Chun-Chen Yang, Taipei (TW); Ching-Fu Wang, Taipei (TW); Chin-Hsun Huang, Taipei (TW); Wei-Cheng Chen, Taipei (TW)

(73) Assignee: NEUROBIT TECHNOLOGIES CO., LTD., Taipei (TW)

( * ) Notice: Subject to any disclaimer, the term of this patent is extended or adjusted under 35 U.S.C. 154(b) by 164 days.

(21) Appl. No.: 16/927,398

(22) Filed: Jul. 13, 2020

(65) Prior Publication Data

US 2022/0007936 A1    Jan. 13, 2022

(51) Int. Cl.

| | |
|---|---|
| A61B 5/00 | (2006.01) |
| A61B 5/0205 | (2006.01) |
| A61B 5/024 | (2006.01) |
| A61B 5/0531 | (2021.01) |
| A61B 5/12 | (2006.01) |
| A61B 5/16 | (2006.01) |
| A61B 5/369 | (2021.01) |
| A61B 5/389 | (2021.01) |
| G16H 50/20 | (2018.01) |

(52) U.S. Cl.
CPC .......... *A61B 5/4041* (2013.01); *A61B 5/0004* (2013.01); *A61B 5/02055* (2013.01); *A61B 5/024* (2013.01); *A61B 5/0531* (2013.01); *A61B 5/121* (2013.01); *A61B 5/165* (2013.01); *A61B 5/369* (2021.01); *A61B 5/389* (2021.01); *A61B 5/443* (2013.01); *A61B 5/4863* (2013.01); *A61B 5/7264* (2013.01); *A61B 5/742* (2013.01); *G16H 50/20* (2018.01); *A61B 2560/02* (2013.01)

(58) Field of Classification Search
None
See application file for complete search history.

(56) References Cited

U.S. PATENT DOCUMENTS

| | | | | |
|---|---|---|---|---|
| 2008/0243005 | A1* | 10/2008 | Jung | G16H 40/67 600/300 |
| 2018/0046773 | A1* | 2/2018 | Tang | G06N 3/044 |
| 2019/0110754 | A1* | 4/2019 | Rao | G06N 20/00 |

* cited by examiner

*Primary Examiner* — Sana Sahand
(74) *Attorney, Agent, or Firm* — Sinorica International Patent & Trademark

(57) ABSTRACT

The present invention provides a neurological disorders decision support system that can assist an examiner to diagnose an examinee. The neurological disorders decision support system includes a user module, a screening module, an intelligent calculation module and a diagnosis module. The user module sends an inquiry to the examinee, receives a response message from the examinee, and retrieves a physiological characteristic signal of the examinee. The screening module executes a neurological examination application program to indicate to the examinee to obtain physiological characteristic signals. The screening module outputs response messages and physiological characteristic signals for the intelligent calculation module to execute an algorithm to generate an analysis report. The analysis report assists the examiner for diagnosis, and sends a diagnosis notification to the user module through the diagnosis module. The invention also provides a neurological disorders decision support method.

13 Claims, 3 Drawing Sheets

DECISION SUPPORT SYSTEM AND METHOD THEREOF FOR NEUROLOGICAL DISORDERS

FIELD OF THE INVENTION

The present invention is related to the technical field of neurological examination device, and, more particularly, to an auxiliary examination method and system for neurological diseases capable of assisting an examiner's diagnosis through artificial intelligence calculation of cranial nerve disease.

SUMMARY OF THE INVENTION

A first objective of the present invention is to provide a neurological disorders decision support system, which performs neurological examination of the cranial nerves of the examinee (for example, a suspected patient) by executing a neurological examination application program.

The second objective of the present invention is based on the above-mentioned neurological disorders decision support system. The examination reports are generated through artificial intelligence calculation of examination data based on big data of cranial nerve diseases and to assist the examiner to make an accurate diagnosis, and then to provide the examinee with the purpose of appropriate treatment.

The third objective of the present invention is based on the above-mentioned neurological disorders decision support system. It can be based on the basic information of the examinee (such as gender, age, place of residence, etc.), medical history data (such as personal pain history, family medical history, electronic medical records, etc.), physiological information (such as eyeball images, eye images, brain wave signals, myoelectric signals, etc.), state of consciousness, etc., to select appropriate neurological examination items.

The fourth objective of the present invention is based on the above-mentioned neurological disorders decision support system. The examinee can be guided to perform specified actions to obtain the physiological characteristic signal of the examinee based on the above-mentioned neurological disorders decision support system. The physiological characteristic signal is used as calculation data for subsequent analysis report generation.

The fifth objective of the present invention is based on the above-mentioned neurological disorders decision support system. The neurological examination application program provides various examination items, and the examinee can perform one or more examinations from various examination items.

The sixth objective of the present invention is based on the above-mentioned neurological disorders decision support system. The artificial intelligence algorithm is used to establish an analysis model related to the examination result, so as to be able to generate an analysis report to assist the examiner for diagnosis.

The seventh objective of the present invention is based on the above-mentioned neurological disorders decision support system. The examiner's diagnosis notification can be sent back to the analysis model again for training so that the analysis report of the artificial intelligence algorithm is closer to the final diagnosis.

The eighth objective of the present invention is based on the above-mentioned neurological disorders decision support system. The intelligent calculation module is installed on a remote server (or cloud) to link one or more screening terminals, such as hospitals, clinics, pharmacies, and home, etc., to achieve artificial intelligence calculation of remote big data.

The ninth objective of the present invention is based on the above-mentioned neurological disorders decision support system. The server and the screening terminal are linked by means of the Internet of Things (IoT). The digital data is encrypted and decrypted during the linking process to achieve the purpose of protecting the privacy of the examinee.

The tenth objective of the present invention is based on the above-mentioned neurological disorders decision support system. The analysis report is generated and transmitted to the medical system for examination and diagnosis by examiners, such as doctors and medical personnel.

The eleventh objective of the present invention is based on the above-mentioned neurological disorders decision support system. The intelligent calculation module can be applied to handheld vehicles, wearable devices, monitors, computers, and tablet computers.

The twelfth objective of the present invention is based on the above-mentioned neurological disorders decision support system. The real-time collection and analysis of data are provided to generate corresponding trend analysis or predictive analysis.

The thirteenth objective of the present invention is based on the above-mentioned neurological disorders decision support system. The data and/or analysis reports are used to share or consolidate to a data platform.

The fourteenth objective of the present invention is to provide a neurological disorders decision support method for neurological diseases, so as to achieve the purpose of assisting an examiner in diagnosing an examinee.

In order to achieve the above objective or other objectives, the present invention provides a neurological disorders decision support system for assisting an examiner to diagnose an examinee. The neurological disorders decision support system comprises a user module, a screening module, an intelligent calculation module, and a diagnosis module. The user module comprises an indication unit and an interface unit. The indication unit is connected to the interface unit. The indication unit is configured to issue an inquiry to the examinee according to a first indication signal and the interface unit configured for the examinee returning a response message according to the inquiry and acquiring a physiological characteristic related to the examinee to generate at least one of a physiological characteristic signal. The screening module is connected to the user module. The screening module generates the first indication signal and outputs the first indication signal to the indication unit, and the screening module executing a neurological examination application program and generating a second indication signal according to the response message to the indication unit, the second indication signal configured to indicate the examinee to perform a corresponding designated action to obtain the physiological characteristic signal from the interface unit. The screening module outputs the response message and the physiological characteristic signal, wherein the neurological examination application program providing a plurality of examination items, the neurological examination application program selecting one or more examination items from the examination items based on the response message. The intelligent calculation module is connected to the screening module. The intelligent calculation module executes an algorithm to calculate at least one of the response message, the physiological characteristic signal and the examination items to generate an analysis report to the examiner.

In order to achieve the above or other objectives, the present invention additionally provides a neurological disorders decision support system for assisting an examiner to diagnose an examinee. The neurological disorders decision support system comprises a user module, a screening module, an intelligent calculation module, and a diagnosis module. The user module comprises an indication unit and an interface unit. The indication unit is connected to the interface unit. The indication unit is configured to issue an inquiry to the examinee according to a first indication signal and the interface unit configured for the examinee returning a response message according to the inquiry and acquiring a physiological characteristic related to the examinee to generate at least one of a physiological characteristic signal. The screening module is connected to the user module. The screening module generates the first indication signal and outputs the first indication signal to the indication unit, and the screening module executing a neurological examination application program and generating a second indication signal according to the response message to the indication unit, the second indication signal configured to indicate the examinee to perform a corresponding designated action to obtain the physiological characteristic signal from the interface unit. The screening module outputs the response message and the physiological characteristic signal, wherein the neurological examination application program providing a plurality of examination items, the neurological examination application program selecting one or more examination items from the examination items based on the response message. The intelligent calculation module is connected to the screening module. The intelligent calculation module executes an algorithm to calculate at least one of the response message, the physiological characteristic signal and the examination items to generate an analysis report. The diagnosis module is connected to the intelligent calculation module and the user module. The diagnosis module receives the analysis report for assisting the examiner for diagnosis, and the examiner sent a diagnosis notification to the user module through the diagnosis module.

In order to achieve the above or other objectives, the present invention additionally provides a neurological disorders decision support method for assisting an examiner to diagnose an examinee. The neurological disorders decision support method comprises a step (a) asking the examinee to obtain a response message from the examinee; step (b) executing a neurological examination application program to analyze the response message, wherein the neurological examination application program provides plural examination items; step (c) the neurological examination application program selecting one or more examination items from the examination items according to the response message to generate an indication signal to indicate to the examinee to perform a corresponding designed action so as to obtain a physiological characteristic signal of the examinee therefrom; step (d) executing an algorithm to generate an analysis report from at least one of the response message, the physiological characteristic signal and the examination items, wherein the algorithm is at least one of a locking algorithm, an adaptive algorithm, a machine learning algorithm and deep learning; and, step (e) providing the analysis report to the examiner.

Compared with the prior art, the present invention provides a neurological disorders decision support system and method that can receive the analysis report generated by the intelligent calculation module to assist the examiner in the diagnosis, and the examiner can send a diagnosis notification to the examiner, medical staff, rescue unit, etc. In one embodiment, the diagnosis notification may also notify the relevant medical institution in advance to prepare for relevant treatment.

BACKGROUND OF THE INVENTION

Traditional neurological examination is very important for early identification and evaluation of patients with cranial nerve diseases and sending patients to appropriate hospitals for follow-up diagnosis and treatment. In addition to consciousness assessment, the most significant is the neurological examination of the second to the eighth pair of cranial nerves. The second to eighth pair of cranial nerves are the optic nerve (e.g., to transmit olfactory information from the nasal cavity to the brain), the oculomotor nerve (e.g., to control eye movements and pupils), the trochlear nerve (e.g., to dominate eye focus), and the trigeminal nerve (e.g., to transmit facial skin perception and dominate chewing), abducens nerve (e.g., to allow the eyeball to move outward), facial nerves (e.g., to control facial expression muscles, to transmit taste messages), and vestibulocochlear nerve (e.g., to transmit auditory and balance sensory messages).

As a part of physical examination, the neurological examination may be easily overlooked in the diagnosis of general diseases, but the importance of neurological examination in the diagnosis of nervous system-related diseases is irreplaceable, such as dementia, stroke, Parkinson's disease, etc. Neurological examination is an auxiliary clinical tool that can help diagnose possible diseases, many items that can be checked at present. However, in practice, the doctor will choose the appropriate test item according to his/her experience and judge whether there is a cranial nerve disease or which type of cranial nerve disease according to the results after the test.

In view of the above, the present invention provides an auxiliary examination system and method for neurological diseases capable of assisting an examiner to diagnose cranial nerve disease and reduce the waste of resources to improve the survival rate and cure rate of the examinee.

DETAILED DESCRIPTION OF THE PREFERRED EMBODIMENTS

In order to fully comprehend the objectives, features, and efficacy of the present invention, a detailed description is described by the following substantial embodiments in conjunction with the accompanying drawings. The description is as below.

Figure 1:
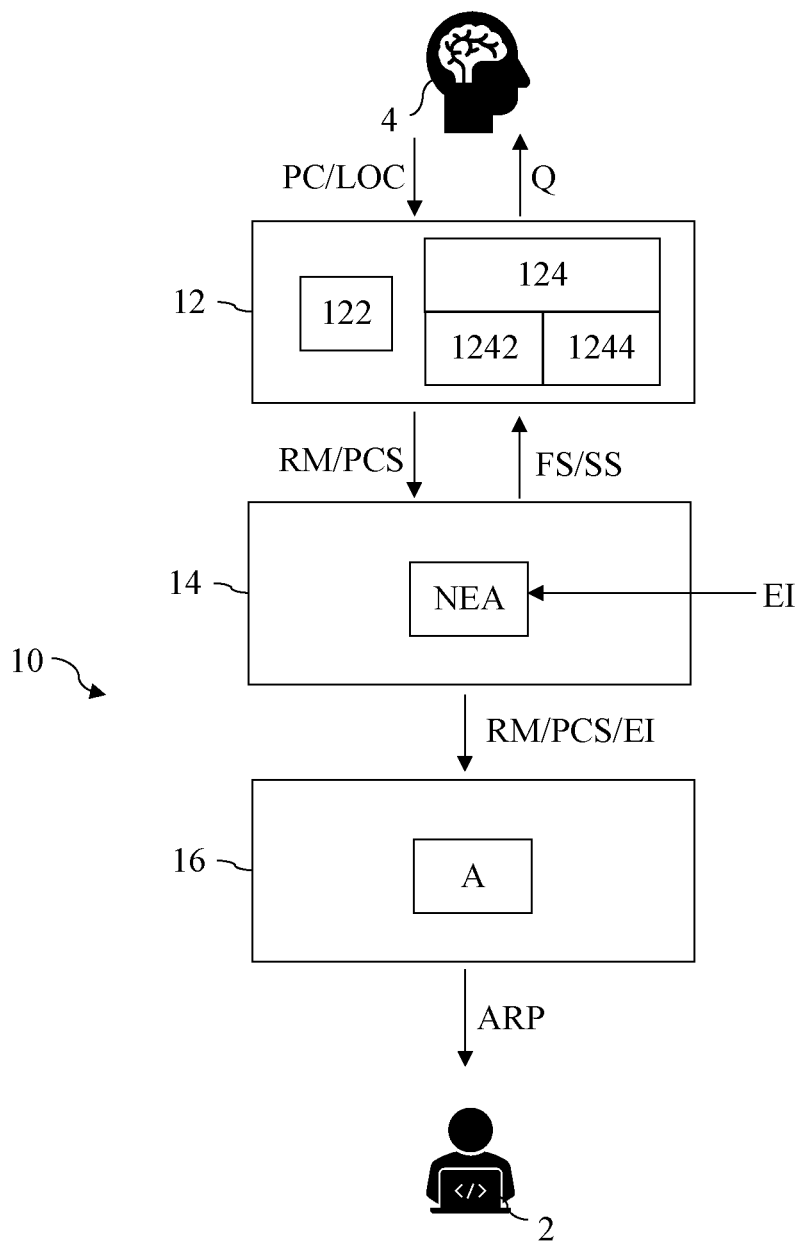
FIG. 1 a block diagram of a neurological disorders decision support system according to the first embodiment of the present invention.

Referring to FIG. 1, a block diagram of the neurological disorders decision support system according to the first embodiment of the present invention. In FIG. 1, a neurological disorders decision support system 10 can assist an examiner 2 to examine an examinee 4. Examiner 2 is a person who has the ability to diagnose diseases and interpret reports and diagnose what type of neurological disease the examinee is suspected of. In another embodiment, the examiner 2 may also be a user of a data platform, and the data platform may receive or aggregate a raw data or processed data generated by the neurological disorders decision support system 10, such as a physiological characteristic PC, a physiological characteristic signal PCS, a response message RM, a physiological characteristic signal PSC, etc., or an analysis report ARP mentioned later.

The platform can be marked by professionals such as physicians and then shared for subsequent research or analysis purposes.

The neurological disorders decision support system 10 includes a user module 12, a screening module 14, and an intelligent calculation module 16.

The user module 12 includes an indication unit 122 and an interface unit 124. The indication unit 122 is connected to the interface unit 124.

The indication unit 122 sends an inquiry Q to the examinee 4 according to a first indication signal FS, wherein the first indication signal FS provides a driving signal to drive the indication unit 122 to generate corresponding indications, for example, the indication unit 122 uses lights, sounds, light, images, etc. to present the aforementioned indications to attract the attention of the examinee 4. Further, the first indication signal FS provides data to send an inquiry Q to the examinee in the indication unit 122, wherein the inquiry Q may be to guide the examinee 4 to provide information, images, identity, body movements, etc. related to the examinee 4.

For example, the indication unit 122 is a liquid crystal display screen. The first indication signal FS drives the liquid crystal display screen and displays the inquiry Q, or the indication unit 122 is a speaker. The first indication signal FS drives the speaker to send out the inquiry Q to the examinee 4.

The interface unit 124 enables the examinee 4 to return a response message RM according to the query Q and retrieve a physiological characteristic PC related to the examinee 4 to generate a physiological characteristic signal PCS. For example, the physiological characteristic PC is a brain Blood oxygen changes, a heartbeat, a breathing, a myoelectric signal, a joint angle, a center of gravity, a gait performance, an Electroencephalograph (EEG), a brain wave, a blood pressure, etc. And, the physiological characteristic signal PCS comes from an eyeball image, an eye image, an eyeball blood vessel volume, an eyeball fluid volume, an eye image, a brain wave, an electromyography, a heart rate, skin moisture, a periocular skin blood vessel flow rate, a body impedance, a hearing, a sound, a body temperature etc. In another embodiment, the interface unit 124 is an input element 1242 and a detection element 1244, for example, the input element 1242 is a microphone, a camera, a touch screen, a keyboard, a mouse, and other electronic elements. And, the detection element 1244 is configured to detect body temperature, an ambient temperature, a humidity, electromyography, an image, a sound, a blood pressure, an expiration/inspiration volume, and other electronic components.

The input element 1242 provides the examinee 4 to input basic data, medical history data, etc., wherein the basic data and/or medical history data input by the examinee 4 can be used as one of the reference factors for the screening module 14 to select appropriate examination item EI, for example, the basic data is gender, age, place of residence, etc. And, for example, the medical history data can be personal pain history, family medical history, electronic medical record, etc.

The detection element 1244 can detect the examinee 4 in an active or passive manner to obtain the physiological characteristic PC and a state of consciousness LOC of the examinee 4, for example, the state of consciousness LOC can be Alert, Drowsy, Stuporous, Comatose, etc. For example, in the passive mode, the detection element 1244 can observe and detect the passive behavior of the examinee 4, that is, the behavior or spontaneous physiological reaction of the examinee 4 itself, so as to obtain the examinee 4 corresponding physiological characteristic signal PCS. In the active mode, if the detection element 1244 wants to obtain the examinee's physiological characteristic signal PCS, it can induce the examinee 4 through the external stimuli (not shown), such as electric shock, heating, cooling, and sound. The examinee 4 can be induced to produce, for example, a physiological response to obtain the physiological characteristic signal PSC and the state of consciousness LOC produced by stimulating the examinee 4.

In another embodiment, the detection element 1244 can detect the physiological characteristic PC of the examinee 4 related to nystagmus of one or both eyes, or, the detection element 1244 can detect the physiological characteristic PC related to the examinee 4, wherein the physiological characteristics are the cornea, the iris, the pupil, the sclera, the conjunctiva, the retina, the choroid, the periocular skin and head tilt angle, etc.

The screening module 14 is connected to the user module 12. The screening module 14 generates a first indication signal FS and outputs it to the indication unit 122. Furthermore, the screening module 14 executes a neurological examination application program NEA and generates a second indication signal SS according to the response message RM and outputs it to the indication unit 122, to indicate the examinee 4 to perform a corresponding designated action or drive the detection element 1244 or the interface unit 124 (or the detection element 1244) to extract the physiological characteristic signal PSC from the examinee 4, wherein the neurological examination application program NEA provides plural examination items EI, and the neurological examination application program NEA selects one or more examination items EI from the examination items EI according to the response message RM. For example, the examination items EI can be a consciousness assessment, a coma index, an Alert Vocal Pain Unresponsive (AVPU) method, a Glasgow Coma Scale (GCS), a Dizziness Handicap Inventory (DHI), a light reflex test, an eye movement, a facial information collection, a facial nerve assessment, a corneal reflex, a blink reflex, a vestibulo-ocular reflex, a The Cincinnati Prehospital Stroke Scale, and an U.S. National Institute of Health Stroke Scale. According to the requirements of different examination items EI, the neurological examination application program NEA will generate different second indication signals SS to guide the examinee 4 to make specified actions or drive the interface unit 124 (or the detection element 1244) hence directly obtaining the corresponding physiological characteristic signal PSC from the examinee 4. In yet another embodiment, the examination items EI can be combined into an examination group so that the neurological inspection application program NEA can select therefrom. Besides, the screening module 14 outputs a response message RM and a physiological characteristic signal PCS.

In another embodiment, in addition to determining which examination item EI is selected by the response message RM, the neurological examination application NEA also determines the examination time, necessary examination items, and priority order of examination items.

The intelligent calculation module 16 is connected to the screening module 14. The intelligent calculation module 16 executes an algorithm A to calculate the response message RM, the physiological characteristic signal PCS, the examination item EI, etc., to generate an analysis report ARP, wherein the algorithm A may adopt, for example, a locking algorithm, an adaptive algorithm, a machine learning algorithm, deep learning, etc. Algorithm A can make an overall prediction based on the results of received messages, signals, and examination items EI by algorithm A with artificial intelligence. Besides, the analysis report ARP may include a raw data and an evaluation content, wherein the raw data that have not been calculated by the algorithm A are the response message RM, and the physiological characteristic signal PSC, etc. And, the evaluation content is the indicators, data, graphics, etc. generated by the calculation of the response message, the physiological characteristic signal, and the examination items by the algorithm A.

For example, the algorithm A calculates a dynamic eyeball image, and obtains correspondingly from the dynamic eyeball image, a nystagmus waveform, a gain value (gain), a phase, a peak velocity, an accuracy, a duration, a phase velocity, a latency, an overshoot, an undershoot and a total harmonic distortion, and then captures a feature value. The feature value is calculated by the machine learning algorithm to determine a disease type so that the disease type is displayed in the analysis report ARP.

In another embodiment, in order to increase the accuracy of the analysis report ARP, the analysis report ARP may be returned to the intelligent calculation module 16 for retraining.

To explain in a situation, the examinee 4 wants to confirm whether he has a neurological disease through the neurological disorders decision support system 10. Therefore, the examinee 4 triggers the screening module 14 through the interface unit 124 of the user module 12, so that the screening module 14 sends an inquiry Q, for example, asking for basic information, Medical history data and current physical condition, such as dizziness, unstable standing, weakness, etc. of the examinee 4 to the indication unit 122 of the user module 12. After the examinee 4 provides the basic data, the medical history data, and the response message RM with the current physical condition through the input element 1242 of the interface unit 124, the screening module 14 executes the neurological examination application program NEA according to the response message RM. The neurological examination application program NEA will select one or more appropriate items from a variety of examination items EI according to the status in the response message RM. The selection of items can be calculated through the neurological examination application program NEA. Based on a hypothesis herein, the neurological examination application program NEA, based on the content of the response message RM, believes that the examination items EI should use the U.S. National Institute of Health Stroke Scale (NIHSS). In the NIHSS scale used by the neurological examination application program NEA, the scale ranges from 0 points of the normal state to 42 points of the brain death state. Since the NIHSS scale needs to check the level of consciousness of the examinee 4, firstly, the second indication signal SS can be generated from the screening module 14 to drive the indication unit 122 to sequentially generate light sound, loud noise, and low-current electric shocks to the examinee 4 and high-current electric shock to the examinee 4. The physiological characteristic signals PSC corresponding to the physiological characteristic PS of the examinee 4 are separately obtained from the detection element 1244. The neurological examination application program NEA further provides scores based on the physiological characteristic signal PSC through, for example, determination of a threshold value. Besides, the second indication signal SS is generated from the screening module 14 again to drive the indication unit 122 to ask the examinee 4 such as the current year, month, and day, the age of the examinee 4, etc. The examinee 4 generates the response message through the input element 1242. The neurological examination application program NEA further determines the score based on the response message RM.

According to the requirements of the NIHSS table, multiple detections of the examinee 4 are performed by the neurological examination application program NEA to obtain the relevant physiological characteristic signal PCS of the examinee 4 required for the NIHSS scale evaluation. Finally, the examinee 4 provides a complete score under the score of the NIHSS scale.

The intelligent calculation module 16 executes the algorithm A to calculate the response message RM, the physiological characteristic signal PCS, the examination item EI, etc. to obtain an analysis report ARP containing graphs, trends, values, etc., and provide it to the Examiner 2.

In another situation, the physiological characteristic PC, physiological characteristic signal PCS, response message RM, physiological characteristic signal PSC, etc. generated or collected by the neurological disorders decision support system 10 can be transmitted to the data platform such as medical platforms, cloud servers, health insurance systems, etc. The data platform can collect data and reports from multiple neurological disorders decision support systems 10 so that the examiner 2 of the data platform can share and use the data. In addition to assisting judgment, it can also be applied to academic research, new drug development, and clinical investigations.

It is worth noting that, in another embodiment, the neurological disorders decision support system 10 further includes a transmission unit (not shown) to ensure the safety of transmission of data (such as the response message RM and the physiological characteristic signal PSC). The transmission unit can be connected to the screening module 14 and the user module 12. Therefore, the transmission unit can execute an encryption procedure to encrypt the response message RM and the physiological characteristic signal PSC, as data is being transmitted between the screening module 14 and the user module 12, to form an encrypted response message RM and physiological characteristic signal PSC. Further, encrypted response message RM and physiological characteristic signal PSC can be reverted back to unencrypted response message RM and physiological characteristic signal PSC through decrypting.

In yet another embodiment, the neurological disorders decision support system 10 may further include an identity verification unit (not shown) connected to the screening module 14, which can verify the identity of the examinee 4.

Figure 2:
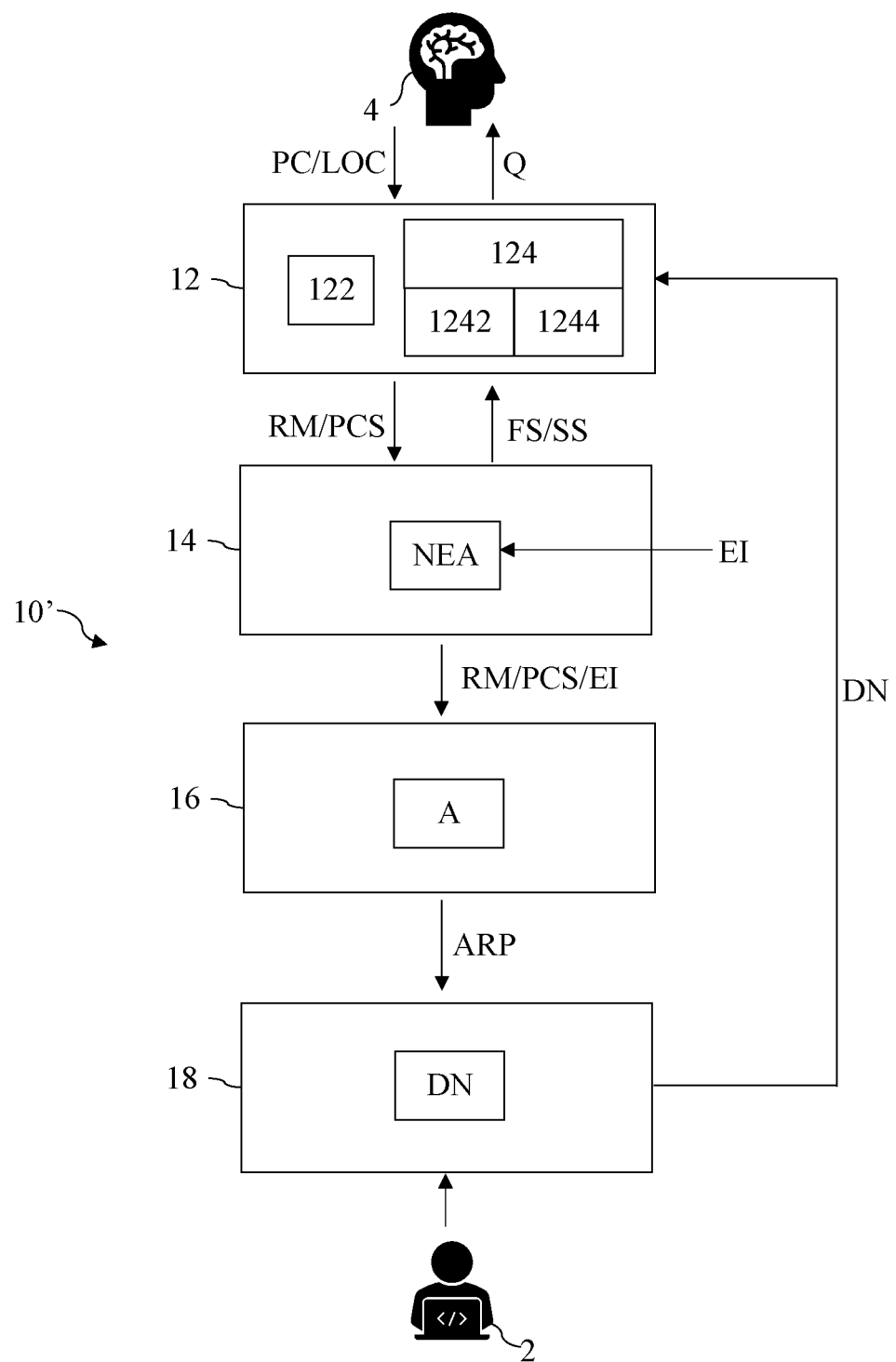
FIG. 2 is a block diagram of the auxiliary examination system for neurological diseases according to the second embodiment of the present invention.

Referring to FIG. 2, illustrate a block diagram of a neurological disorders decision support system according to a second embodiment of the present invention. In FIG. 2, a neurological disorders decision support system 10' further includes a diagnosis module 18 in addition to the user module 12, the screening module 14, and the intelligent calculation module 16 of the first embodiment.

Description of user module 12, screening module 14, and intelligent calculation module 16 is the same as the description for such in the first embodiment and hence is not to be repeated here.

The diagnosis module 18 is connected to the intelligent calculation module 16 and the user module 12. The diagnosis module 18 receives the analysis report ARP to assist the examiner 2 for diagnosis, and the examiner 2 sends a diagnosis notification DN to the user module 12 through the diagnosis module 18.

Following the aforementioned scenario, the examiner 2 can obtain the analysis report ARP through the diagnosis module 18, and judge from the analysis report ARP and the examiner 2's own experience. The examiner 2 will send a diagnosis notification DN to the examinee 4 to realize that the analysis report ARP can assist the examiner in the auxiliary examination of neurological diseases.

In another embodiment, in order to increase the accuracy of the analysis report ARP, the diagnosis notification DN of the examiner 2 may be returned to the intelligent calculation module 16 for retraining.

Figure 3:
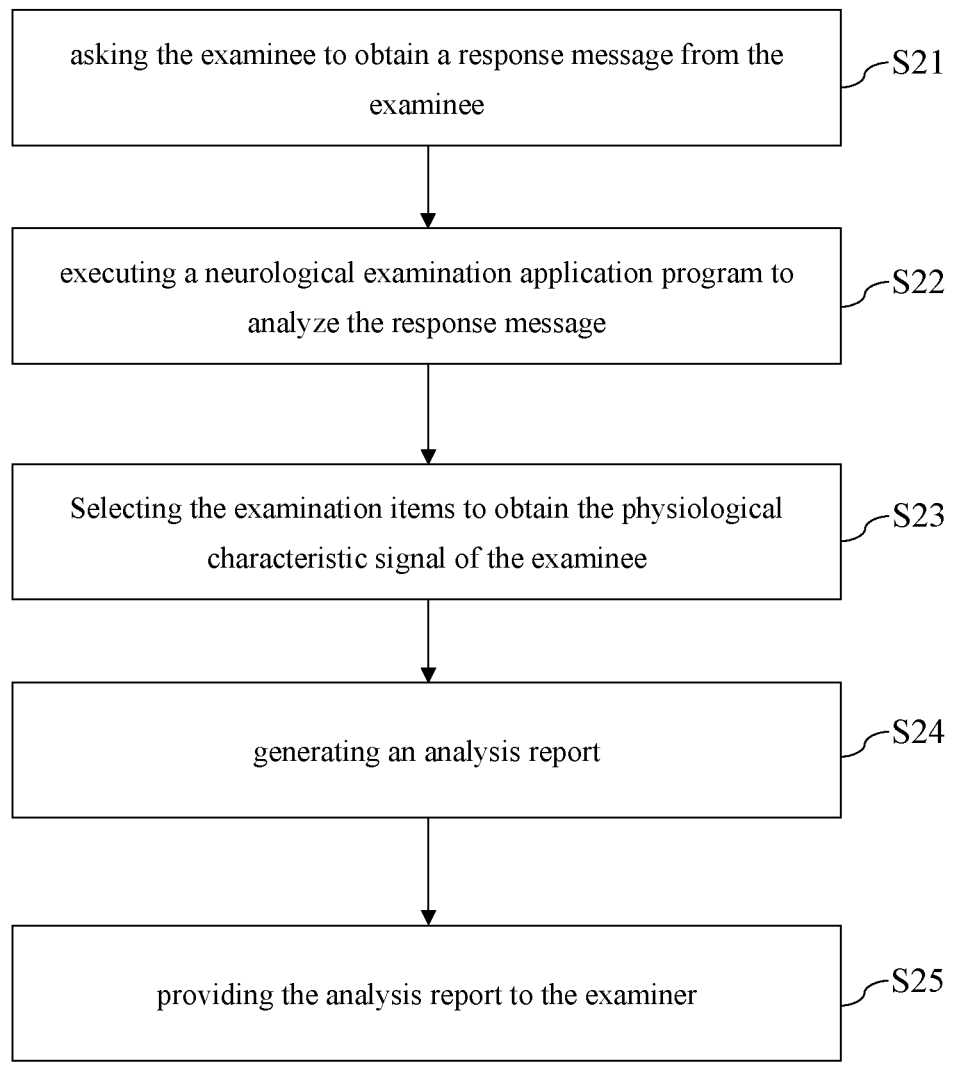
FIG. 3 is a schematic flow diagram of the auxiliary examination method for neurological diseases according to the third embodiment of the present invention.

Referring to FIG. 3, a schematic flow chart of the auxiliary examination method for neurological diseases according to the third embodiment of the present invention. In FIG. 3, an auxiliary examination method for neurological diseases can assist an examiner to examine an examinee.

The auxiliary examination method for neurological diseases starts at step S21. In Step S21, the method is to ask the examinee to obtain a response message from the examinee.

In step S22, a neurological examination application program is executed to analyze the response message. Wherein, the neurological examination application program provides plural examination items.

In step S23, the neurological examination application program selects one or more examination items from the examination items according to the response message to generate an indication signal to indicate the examinee to obtain a physiological characteristic signal of the examinee. In another embodiment, this step further includes detecting a spontaneous physiological response of the examinee or detecting a physiological reaction of the examinee induced to generate the physiological characteristic signal.

In step S24, the method is to execute an algorithm to generate an analysis report from at least one of the response message, the physiological characteristic signal and the examination items. Wherein, the algorithm is at least one of a locking algorithm, an adaptive algorithm, a machine learning algorithm and a deep learning algorithm.

In step S25, the analysis report is provided to the examiner, for example, the examiner diagnoses the examinee with the analysis report to send a diagnosis notification to the examinee. In another step, the diagnosis notification can be used to train the algorithm.

It is worth noting that each of the above steps further includes a step of performing an encryption procedure to encrypt at least one of the response message and the physiological characteristic signal to form the encrypted response message and the physiological characteristic signal.

The present invention has been disclosed in a preferred embodiment above. However, those skilled in the art should understand that the embodiment is only used to describe the present invention and should not be construed as limiting the scope of the present invention. It should be noted that all changes and substitutions equivalent to the embodiment should be included in the scope of the present invention. Therefore, the protection scope of the present invention should be defined by the scope of the patent application.

ITEM LEGEND

2 . . . examiner
4 . . . examinee
10-10' . . . neurological disorders decision support system
12 . . . user module
122 . . . indication unit
124 . . . interface unit
1242 . . . input element
1244 . . . detection element
14 . . . screening module
16 . . . intelligent calculation module
18 . . . diagnosis module
FS . . . first indication signal
Q . . . inquiry
RM . . . response message
PC . . . physiological characteristic
PCS . . . physiological characteristic signal
LOC . . . state of consciousness
NEA . . . neurological examination application program
SS . . . second indication signal
ARP . . . analysis report
A . . . algorithm
DN . . . diagnosis notification
S21-S25 . . . step

What is claimed is:

1. A neurological disorders decision support system for assisting an examiner to diagnose an examinee, the neurological disorders decision support system comprising:
a user module comprising an indication unit and an interface unit, the indication unit connected to the interface unit and configured to issue an inquiry to the examinee according to a first indication signal, and the interface unit configured for the examinee to return a response message according to the inquiry and configured to acquire a physiological characteristic related to one or both eyes of the examinee to generate a physiological characteristic signal, wherein the interface unit is an input element and a detection element, the input element providing at least one of an input basis data and a medical history data of the examinee, and the detection element detecting the examinee to obtain the physiological characteristic and a consciousness state of the examinee;
a screening module connected to the user module, the screening module configured to generate the first indication signal and output the first indication signal to the indication unit, and the screening module further configured to execute a neurological examination application program and generate a second indication signal according to the response message to the indication unit, wherein the second indication signal is configured to indicate to the examinee to perform a corresponding designated action to obtain the physiological characteristic signal from the interface unit, and the screening module is further configured to output the response message and the physiological characteristic signal, and wherein the neurological examination application program provides a plurality of examination items and selects one or more examination items from the plurality of examination items based on the response message;
an intelligent calculation module connected to the screening module, the intelligent calculation module configured to execute an algorithm to calculate at least one of the response message, the physiological characteristic signal and the examination items to generate an analysis report to the examiner; and a diagnosis module connected to the intelligent calculation module and the user module, the diagnosis module configured to receive the analysis report for assisting the examiner for diagnosis and send a diagnosis notification to the user module, wherein the diagnosis notification is returned to the intelligent calculation module, and the intelligent calculation module is retrained by the diagnosis notification based on the examination items.

2. The neurological disorders decision support system of claim 1, wherein the detection element is configured to detect a spontaneous physiological response of the examinee or the detection element is configured to detect a physiological response generated by inducing the examinee to generate the physiological characteristic signal and confirm the consciousness state.

3. The neurological disorders decision support system of claim 1, wherein the detection element is configured to detect the physiological characteristic of the examinee with nystagmus related to the one or both eyes of the examinee.

4. The neurological disorders decision support system of claim 1, wherein the detection element is configured to detect the physiological characteristic of at least one of a cornea, an iris, a pupil, a sclera, a conjunctiva, a retina, a choroid, a periocular skin area of the eye and a head tilt angle of the examinee.

5. The neurological disorders decision support system of claim 1, wherein the physiological characteristic signal comes from at least one of an eyeball image, an eye image, an eyeball blood vessel flow rate, an eyeball fluid volume, a brain wave, an electromyography, a heart rate, a skin water content, a periocular skin blood vessel flow rate, a body impedance, a hearing and a body temperature.

6. The neurological disorders decision support system of claim 1, wherein the examination items are at least one of a consciousness assessment, a coma index, an Alert Vocal Pain Unresponsive (AVPU) method, a Glasgow Coma Scale (GCS), a Dizziness Handicap Inventory (DHI), a light reflex test, an eye movement, a facial information collection, a facial nerve assessment, a corneal reflex, a blink reflex, a head eye reflex, a Cincinnati Prehospital Stroke Scale and a U.S. National Institute of Health Stroke Scale.

7. The neurological disorders decision support system of claim 6, wherein the examination items are combined into an examination group and configured for being chosen by the neurological examination application program.

8. The neurological disorders decision support system of claim 1, further comprising a transmission unit connected to at least one of the screening module and the user module, wherein the transmission unit executes an encryption procedure to encrypt at least one of the response message and the physiological characteristic signal to form the encrypted response message and the encrypted physiological characteristic signal.

9. The neurological disorders decision support system of claim 1, further comprising an identity verification unit connected to the screening module for verifying the identity of the examinee.

10. The neurological disorders decision support system of claim 1, wherein the algorithm is at least one of a locking algorithm, an adaptive algorithm, a machine learning algorithm and a deep learning algorithm.

11. The neurological disorders decision support system of claim 10, wherein the algorithm calculates a dynamic eyeball image, and correspondingly obtains at least one of a nystagmus waveform, a gain value (gain), a phase, a peak velocity, an accuracy, a duration, a phase velocity, a latency, an overshoot, an undershoot and a total harmonic distortion from the dynamic eyeball image, and then captures a feature value, and wherein the feature value is calculated by the machine learning algorithm to determine a disease type so that the disease type is displayed in the analysis report.

12. The neurological disorders decision support system of claim 1, wherein the analysis report includes a raw data and an evaluation content, wherein the raw data is at least one of the response message and the physiological characteristic signal that has not been calculated by the algorithm, and the evaluation content is an indicator, a data and a graphic generated after the algorithm calculates at least one of the response message, the physiological characteristic signal and the examination items.

13. The neurological disorders decision support system of claim 1, wherein the intelligent calculation module is further retrained by the diagnosis notification based on at least one of the response message and the physiological characteristic signal.

* * * * *